(12) United States Patent
Tom-Moy et al.

(10) Patent No.: US 7,488,607 B2
(45) Date of Patent: Feb. 10, 2009

(54) ELECTRONICALLY READABLE MICROARRAY WITH ELECTRONIC ADDRESSING FUNCTION

(75) Inventors: May Tom-Moy, San Carlos, CA (US); Carl Myerholtz, Cupertino, CA (US); August Hidalgo, San Fancisco, CA (US); William McAllister, Saratoga, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 143 days.

(21) Appl. No.: 10/676,707

(22) Filed: Sep. 30, 2003

(65) Prior Publication Data
US 2005/0079505 A1 Apr. 14, 2005

(51) Int. Cl.
*G01N 33/551* (2006.01)
*G01N 33/553* (2006.01)

(52) U.S. Cl. ............... 436/524; 422/82.01; 422/82.02; 435/6; 435/287.2; 435/973; 436/149; 436/525; 436/527; 436/806; 436/809; 436/815; 436/817

(58) Field of Classification Search ............... 435/7.1, 435/287.1–287.2, 287.9, 288.4, 973; 436/149, 436/806; 422/68.1, 82.01, 82.02
See application file for complete search history.

(56) References Cited

U.S. PATENT DOCUMENTS

| | | | | |
|---|---|---|---|---|
| 3,930,823 A * | 1/1976 | Kurtz et al. | | 65/33.6 |
| 4,789,628 A * | 12/1988 | Nayak | | 435/7.94 |
| 5,132,242 A * | 7/1992 | Cheung | | 436/501 |
| 5,312,762 A * | 5/1994 | Guiseppi-Elie | | 205/778 |
| 5,532,128 A | 7/1996 | Eggers et al. | | |
| 5,866,321 A | 2/1999 | Matsue et al. | | |
| 5,891,630 A * | 4/1999 | Eggers et al. | | 435/6 |
| 6,535,822 B2 | 3/2003 | Mansky et al. | | |
| 6,545,758 B1 * | 4/2003 | Sandstrom | | 356/317 |
| 6,660,533 B2 * | 12/2003 | Mallet et al. | | 436/518 |

OTHER PUBLICATIONS

Park et al. Array-based electrical detection of DNA with nanoparticle probes. Science (2002), vol. 295, pp. 1503-1505.*
Fluke Corporation. Model 187 & 189 True RMS Multimeter Users Manual, 2002, pp. 2-4, 2-17, 3-6, and 3-7.*
Kittlesen et al., J. Am. Chem Soc., vol. 106, pp. 7389-7396 (1984).

* cited by examiner

*Primary Examiner*—Christopher L Chin (57) ABSTRACT

Methods and apparatus for electronically addressing and interrogating microarrays are disclosed. The described microarrays include a plurality of features disposed on a substrate. Each of the features has a first electrode disposed on the substrate, a second electrode disposed on the substrate, and a probe disposed between the first electrode and second electrode. The substrate also includes addressing circuitry in operable relation to the features. Method of using the microarrays are also described.

19 Claims, 2 Drawing Sheets

ELECTRONICALLY READABLE MICROARRAY WITH ELECTRONIC ADDRESSING FUNCTION

RELATED APPLICATION

Related subject matter is disclosed in U.S. patent application entitled "Detection of Molecular Binding Events", Ser. No. 10/676,957 filed in the names of Myerholtz et al. on the same day as the present application and which is incorporated herein by reference in its entirety, provided that, if a conflict in definition of terms arises, the definitions provided in the present application shall be controlling.

FIELD OF THE INVENTION

The invention relates generally to microarrays, such as polynucleotide microarrays (for example, DNA microarrays), which are useful in diagnostic, screening, gene expression analysis, and other applications. More specifically, the invention relates to electronically addressing and interrogating microarrays.

BACKGROUND OF THE INVENTION

Biomolecular arrays (such as DNA, RNA, peptide, or protein microarrays) are known and are used, for example, as diagnostic or screening tools. Such microarrays include regions of usually different sequence biomolecules (such as polynucleotides or polypeptides) arranged in a predetermined configuration on a substrate. These regions (sometimes referenced as "array features") are positioned at respective locations ("addresses") on the substrate. Biomolecular arrays typically are fabricated on planar substrates either by depositing previously obtained biomolecules onto the substrate in a site specific fashion or by site specific in situ synthesis of the biomolecules upon the substrate. The microarrays, when exposed to a sample, will undergo a binding reaction with the sample and exhibit an observed binding pattern. This binding pattern can be detected upon interrogating the microarray. For example all biomolecule targets (for example, DNA) in the sample can be labeled with a suitable label (such as a fluorescent compound), and the label then can be accurately observed (such as by observing the fluorescence pattern) on the microarray after exposure of the microarray to the sample. Assuming that the different biomolecule targets were correctly deposited in accordance with the predetermined configuration, then the observed binding pattern will be indicative of the presence and/or concentration of one or more components of the sample.

Alternative methods of sensing binding events are being developed. One such method involves electrical detection of binding to probe DNA bound to a surface between two electrodes. See Park et al., Science (2002) 295:1503-1506. Park et al. have reported using a sandwich hybridization to close microelectrode gaps to detect binding of target DNA to probe DNA. In the reported method, probe DNA is immobilized between two microelectrodes spaced 20 microns apart, and then target DNA is hybridized to the probe DNA. Park et al. complete the sandwich hybridization using a third DNA molecule conjugated to gold nanoparticles. To complete the process, a silver stain is applied, resulting in bridging of the gap between the two microelectrodes with deposited silver. The probe/target binding event is then detected as a drop in resistance from the open circuit (>200 megohms) to a closed circuit (<~500 ohms).

The sandwich hybridization method used by Park et al. requires that the target DNA have two recognition elements: one recognition element that is complementary to the probe DNA, and another recognition element that is complementary to the third DNA molecule (conjugated to the gold nanoparticle). This requirement for two recognition elements in the target DNA potentially limits the utility of the method. Additionally, the silver stain used to develop the deposited gold nanoparticles was observed to cause the particles to grow at different rates; this was interpreted as resulting from catalysis of silver deposition by the already deposited silver. Also, during the developing reaction, the silver solution had to be replaced every 2 to 3 minutes to avoid formation of silver particulates in solution. This may be inconvenient in terms of practical use of the method.

U.S. Pat. No. 6,403,317 to Anderson, granted Jun. 11, 2002 describes a method of detecting locations on a nucleic acid probe microarray at which hybridization occurs between targets in a fluid sample and nucleic acid probes disposed on a surface of the nucleic acid probe microarray. The referenced patent describes measuring the temperature at a plurality of discreet locations on the surface of the probe microarray while applying an oscillating level of energy to the probe microarray, thereby causing the temperature of the probe microarray to oscillate.

U.S. patent application Ser. No. 09/915,044, filed on Jul. 24, 2001, teaches the use of a redox active moiety that is associated with an electrode to detect, by means of the electrode, corresponding responses produced as a result of the activation of the redox active moiety. The magnitude of the corresponding response indicates the presence or absence of the target molecule in the sample.

What is needed is an improved method of detection of binding events that provides increased ease of use and utility.

SUMMARY OF THE INVENTION

The invention addresses the aforementioned deficiencies in the art, and provides methods and apparatus for electronically addressing and interrogating microarrays and, more particularly, microarrays having integrated electronic addressing circuitry. A microarray provided in accordance with the present invention includes a plurality of features disposed on a substrate. Each of the features of the microarray has a first electrode disposed on the substrate, a second electrode disposed on the substrate, and a probe disposed between the first electrode and second electrode. The substrate typically comprises a non-conductive material that is suitably inert to the conditions of use and/or manufacture of the microarray. The substrate also includes addressing circuitry in operable relation to the features.

In use of the microarray, the integrated addressing circuitry allows selection of individual features (or subsets of features) to be interrogated. In use, the microarray is contacted with a sample containing one or more targets, e.g. a target polynucleotide, under conditions and for a time sufficient to allow a target to bind to its respective probe (e.g. a polynucleotide complementary to the target) on the microarray. An enhancement reaction is then applied to result in a change in an observable property of the feature of the microarray. The observable property is then monitored using measurement circuitry operably associated with the features of the microarray; such measurement circuitry may be integrated on the substrate in some embodiments. Typically, features of the microarray are adapted to recognize different targets (e.g. the identity of the probe varies from one feature to another on a given microarray), allowing multiplex analysis of multiple different targets using a single array.

In particular embodiments, the microarray has features in which the probe is supported on a pad of resistive material that is adjacent the first electrode and the second electrode. The pad may comprise any resistive material that is suitably inert to the conditions of use and/or manufacture of the device. In certain embodiments, one or both electrodes are in direct contact with the pad. In some embodiments, a gap is defined between one or both electrodes and the pad. In certain embodiments, a microarray provided according to the invention includes a plurality of features supported in an array format on a single substrate, wherein the substrate includes addressing circuitry capable of selectively addressing individual features or groups of features. Certain embodiments further include optional circuitry for interrogating the features of the microarray, optionally including circuitry for accumulation and storage of data about each feature of the microarray. In particular embodiments, one or more conductive traces associated with each feature may be disposed on the substrate electrically connecting electrodes of each feature to addressing circuitry located on the substrate.

The invention also provides methods of detecting a target. A microarray having a plurality of features is contacted with a sample suspected of containing the target, wherein each feature of the microarray comprises a first electrode disposed on a substrate, a second electrode disposed on the substrate, and a probe disposed between the first electrode and second electrode. The substrate includes integrated addressing circuitry in operable relation to the features. In particular embodiments, each feature of the microarray includes a pad of resistive material disposed on the substrate between the first electrode and the second electrode, and the probes are supported on the pad. The target is labeled with a label, and an enhancement reaction is applied to the label. The enhancement reaction typically includes contacting the label with an enhancement reagent (e.g. a source of metal ions) to result in deposition of metal at the label, and removing the enhancement reagent from the label prior to interrogation of the feature. A signal is then delivered to the addressing circuitry to select a feature or group of features to be interrogated. The binding of target at the probe is then detected by measuring an observable property, e.g. an electrical property such as resistance, between the electrodes of the feature(s) that was selected. The enhancement reaction provides a change in the observable property indicating presence of the target. Another signal may then be delivered to the addressing circuitry to select another feature, and so on repeatedly until the desired features of the microarray have been interrogated. Each feature of the microarray may be selectively addressed to detect, by means of the electrodes of the selected feature, corresponding changes in the observable property produced as a result of the presence of labeled and enhanced target bound to the probe disposed between the electrodes. The magnitude of the corresponding changes provides information about the target in the sample, e.g. presence (or absence), concentration, identity or other information. Each feature may have a different probe disposed between the electrodes of the feature, thus enabling a plurality of different targets to be analyzed on a single microarray. In an embodiment, the label includes a gold nanoparticle (or silver nanoparticle) that nucleates the deposition of a metal (e.g. more gold) during the enhancement reaction; the deposited metal alters the electrical property. In various embodiments the label is attached to the target via a conjugate binding pair, such as biotin-avidin.

The substrate of the microarray may comprise a semiconductor substrate having an integrated circuit (IC). The integrated circuit may thus include addressing circuitry for addressing specific features of the microarray, similar to well known addressing circuitry used in random access memory (RAM) technology. The addressing circuitry typically allows a large number of electrodes to be specifically addressed through a relatively small number of externally accessible leads. The integrated circuit may provide measurement circuitry in operable relation to the addressing circuitry, the measurement circuitry operable to measure an observable property, such as resistance between the first and second electrodes, of a selected feature on the microarray. Appropriate conductive elements, such as wires or conductive traces, may be employed to communicate between the circuitry and each feature individually so that the measurement of the observable property at each feature may be accomplished. Similarly, conductive elements may be employed to receive a response from each feature. Such conductive elements may provide an address bus in electrical communication with the addressing circuitry, a data bus in electrical communication with measurement circuitry, or a combined address and data bus.

Additional electronic components may be operably associated with the microarray. As an example, a conventional computer having a microprocessor, storage apparatus, and input and/or output apparatus may have an interface communicating with a microarray to control the addressing and interrogation of the features on the microarray and to record the results. The additional electronic components may be part of the substrate or may be remote from the substrate, or both.

Additional objects, advantages, and novel features of this invention shall be set forth in part in the descriptions and examples that follow and in part will become apparent to those skilled in the art upon examination of the following specifications or may be learned by the practice of the invention. The objects and advantages of the invention may be realized and attained by means of the instruments, apparatus, combinations and methods particularly pointed out in the appended claims.

BRIEF DESCRIPTION OF THE DRAWINGS

These and other features of the invention will be understood from the description of representative embodiments of the method herein and the disclosure of illustrative apparatus for carrying out the method, taken together with the Figures, wherein FIG. 1 schematically illustrates a single feature of an embodiment of a microarray according to the present invention.

To facilitate understanding, identical reference numerals have been used, where practical, to designate corresponding elements that are common to the Figures. Figure components are not drawn to scale.

DETAILED DESCRIPTION

Before the invention is described in detail, it is to be understood that unless otherwise indicated this invention is not limited to particular materials, reagents, reaction materials, manufacturing processes, or the like, as such may vary. It is also to be understood that the terminology used herein is for purposes of describing particular embodiments only, and is not intended to be limiting. It is also possible in the present invention that steps may be executed in different sequence where this is logically possible. However, the sequence described below is preferred.

It must be noted that, as used in the specification and the appended claims, the singular forms "a," "an" and "the" include plural referents unless the context clearly dictates otherwise. Thus, for example, reference to "a probe" includes a plurality of probes. In this specification and in the claims that follow, reference will be made to a number of terms that shall be defined to have the following meanings unless a contrary intention is apparent:

"Supported", "supported on", "supports" or "supporting" includes either being supported (or supporting) in direct contact or indirect contact such that, for example, a first material supported on a second material includes embodiments where the first material is directly contacting the second material and embodiments where one or more intermediate materials are disposed between the first and second materials provided that each intermediate material is bound to the immediately adjacent material so the first material is indirectly bound to the second material. "Integrated" as used herein with reference to a microarray having integrated addressing circuitry means that the microarray and addressing circuitry are in the form of a single unit, i.e. form a unitary component with both addressing circuitry and an array of microarray features as described herein. In relation to position of a probe on an array, a probe is considered to be "disposed between" a first electrode and a second electrode of a feature if the probe is located such that metal deposited near the probe during the enhancement process results in a measurable change in an observable property of the feature as disclosed herein.

A "microarray", unless a contrary intention appears, includes any one, two, or three dimensional arrangement of addressable regions bearing a particular chemical moiety or moieties (called "probes", or "probe molecules") (for example, polynucleotide sequences) associated with that region. A "bioarray" is a microarray of biomolecules, and is sometimes referenced as a "biomolecular array". A microarray is "addressable" in that it has multiple regions of different moieties (for example, different polynucleotide sequences) such that a region (a "microarray feature" or "spot" of the microarray) at a particular predetermined location (an "address") on the microarray will detect a particular target or class of targets (although a microarray feature may incidentally detect non-targets of that microarray feature). In the case of a microarray, the "target" will be referenced as a moiety in a mobile phase (typically fluid), to be detected by probes (sometimes referenced as "target probes") which are supported on the substrate at the various regions. The probes may be supported on the substrate by interactions that include, for example, covalent and/or electrostatic interactions. However, either of the "target" or "target probes" may be the one which is to be evaluated by the other (thus, either one could be an unknown mixture of polynucleotides to be evaluated by binding with the other). "Addressable collection of probes" refers to the multiple regions of different moieties supported by or intended to be supported by the microarray surface. While probes and targets of the present invention will typically be single-stranded, this is not essential. A "target solution" (also referred to as a "sample" or "sample solution") references a mobile phase comprising the target. "Interrogating" the microarray refers to obtaining information from the microarray, especially information about targets binding to the microarray. "Hybridization assay" references a process of contacting a microarray with a mobile phase containing target. An "array format" refers to one or more characteristics of the microarray, such as microarray feature position, microarray feature size, or some indication of a moiety at a given location, including multiple different moieties, each moiety at a different addressable location. A "microarray substrate" refers to an article that supports an addressable collection of probes. The portion of the surface on which the collection of probes is disposed in an addressable format is referenced as the "microarray surface." Of particular interest are DNA microarrays consisting of short DNA oligonucleotides or longer cDNAs attached to a surface in a spatially addressable manner. A target nucleic acid sequence can then be interrogated making use of the inherent property of nucleic acids to form hydrogen-bonded duplexes, e.g. according to Watson and Crick base-pairing rules.

"Biomolecule" refers to types of molecules generally derivable from living organisms, or analogues thereof. Biomolecules include, e.g. amino acids, oligopeptides, polypeptides, glycoproteins, nucleotide monomers, oligonucleotides, polynucleotides, saccharides, polysaccharides, hormones, growth factors, peptidoglycans, or the like. The term "biomolecular fluid" refers to any fluid that comprises biological fluids, biomolecules, and/or other biological substances or materials. Some examples of biological fluids include blood, plasma, serum, solutions containing proteins or nucleic acids, urine, cerebral spinal fluid, saliva, enzymatic mixtures, and other related substances and fluids that are well known in the analytical and biomedical art. An "oligopeptide" is a molecule containing from 2 to about 100 amino acid subunits. "Polypeptide" refers to a molecule having any number of amino acid subunits. An "oligonucleotide" is a molecule containing from 2 to about 100 nucleotide subunits. "Polynucleotide" refers to a molecule having any number of nucleotide subunits. "Analogues" refer to molecules having structural features that are recognized in the literature as being mimetics, derivatives, having analogous structures, or other like terms, and include, for example, polynucleotides incorporating non-natural (not usually occurring in nature) nucleotides, non-natural nucleotide mimetics such as 2'-modified nucleosides, peptide nucleic acids, oligomeric nucleoside phosphonates, polypeptides incorporating non-natural amino acids, and any biomolecule that has added substituent groups, such as protecting groups or linking moieties.

A "conjugate binding pair" refers to two molecules or moieties which bind specifically to each other, generally with a high enough affinity to stay bound throughout the relevant portions of the assay, and which serves as a part of the label or serves to link the label to the target. Depending on the conjugate binding pair, the members (the molecules or moieties) may dissociate under some conditions of the method (i.e. there may be a separate dissociation step). Some examples of conjugate binding pairs include the biotin-streptavidin pair and the digoxigenin-antidigoxigenin pair (Kessler, Advances in Mutagenesis, Berlin/Heidelber; Springer-Verlag; 105-152 (1990)). In certain embodiments of the present invention, a conjugate binding pair is used in binding a label to the target. As an example, for the biotin-streptavidin pair, the biotin would be attached (directly or via a suitable linker moiety) to the target (for a polynucleotide target, the biotin may be attached, for example, via the C5 position of pyrimidines or the C8 position of purines), and the label (e.g. gold nanoparticle or silver nanoparticle) would be conjugated to the streptavidin molecule. For the digoxigenin-antidigoxigenin pair, the digoxigenin hapten moiety would be attached to the target (e.g. via a chain-terminating nucleotide for a polynucleotide target) and the label would be associated with the antidigoxigenin. It will be appreciated by those of skill in the art that moieties having very similar structures and functions to those named above may also be employed as members of conjugate binding pairs: representative examples include avidin, streptavidin, acetylated avidin, acetylated streptavidin, succinylated avidin, succinylated streptavidin, genetically engineered avidin with intact biotin binding sites, genetically engineered streptavidin with intact biotin binding sites, modified avidin with intact biotin binding sites, and modified streptavidin with intact biotin binding sites; as used herein, "biotin-avidin" encompasses such moieties having very similar structures and functions of conjugate binding pairs. Phenylboronic acid complexes may also be used for preparing other high affinity conjugate binding pairs (U.S. Pat. No. 5,594,151). In certain embodiments, the conjugate binding pair may comprise two complementary nucleic acid molecules.

"Resistive", as used herein in referring to a "resistive pad" or a "pad of resistive material", means that the pad resists the flow of electric current through the material. "Non-conductive", as used herein, e.g. when referring to a non-conductive material, means that essentially no electric current flows through the material. In normal use of certain embodiments of a device according to the present invention, less than about 0.5% (typically less than about 0.1%) of the electrical current flow between the first electrode and the second electrode flows through any non-conductive material present (such as the substrate). "Resistance" has the conventional meaning in the electrical arts of resisting flow of electrical current.

A substrate material is defined to be non-conductive when the measured resistance between two electrodes of a test apparatus is greater than about 100 megohms. The test apparatus includes two electrodes disposed on a planar surface of an exemplar of the substrate material, each electrode about 100 micrometers in length, about 20 micrometers wide, and about 1 micrometer thick. The exemplar should be at least 1 millimeter thick, 10 millimeters wide, and 10 millimeters long, with the electrodes located generally near the center of the planar surface. The electrodes of the test apparatus are parallel to each other along their long axes, and the distance between the parallel electrodes is about 20 micrometers. It should be noted that there is no pad of resistive material disposed between the two electrodes on the test apparatus. The electrodes of the test apparatus are arranged to define two opposing sides of a rectangular portion of the exemplar surface about 100 micrometers by about 20 micrometers disposed between the two electrodes. The resistance measurement is made by first drying the substrate and electrodes and then measuring with a suitable ohmmeter. Resistance measurements referred to herein refer to direct current resistance to an applied potential, typically less than about 100 volts, more typically less than about 20 volts, and typically greater than about 1 millivolt, more typically greater than about 20 millivolts.

A "gap" as used herein references a feature defined by an electrode (on one side of the gap) and a pad (on the other side of the gap). A "fissure" as used herein references a feature defined by a first portion (or "segment") of a pad and a second portion ("segment") of the pad. Gaps and fissures may be described as grooves disposed between the electrode(s) and/or pad (or segments of the pad).

Figure 1:
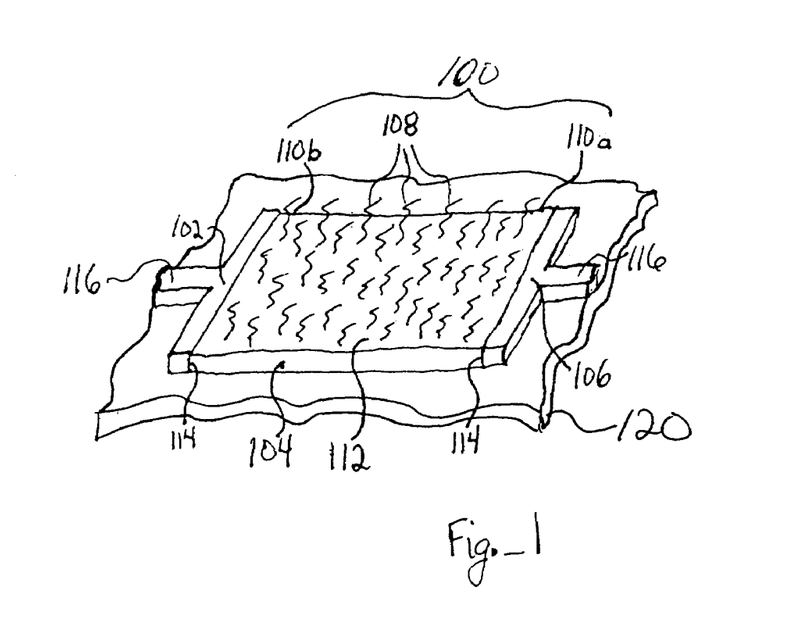

Referring now to the figures, FIG. 1 illustrates a single feature 100 of a microarray according to the present invention. The feature 100 of a microarray according to the present invention includes a first electrode 102 disposed on a substrate 120, a pad 104 of resistive material disposed on the substrate 120 adjacent the first electrode 102, a second electrode 106 disposed on the substrate 120 adjacent the pad 104, and a probe 108 supported on the pad 104. In the embodiment illustrated in FIG. 1, the pad 104 is disposed between the first electrode 102 and second electrode 106 such that the electrodes 102, 106 are located at opposing ends 110a, 110b of the pad 104. In varying embodiments the microarray may be designed with electrodes adjacent the pad at positions other than at opposing ends. In other embodiments, the pad 104 of resistive material is optional, and in embodiments lacking the pad 104, the probe is supported on the substrate 120 at a position generally between the first electrode 102 and second electrode 106. Again referring to FIG. 1, the pad 104 has a surface 112 that supports the probe 108. In the embodiment shown in FIG. 1, the pad 104 is a single planar structure which is bonded to or in direct physical contact with (at site 114) the first electrode 102 and the second electrode 106 such that the pad is in electrical communication with the first electrode 102 and the second electrode 106.

Figure 2:
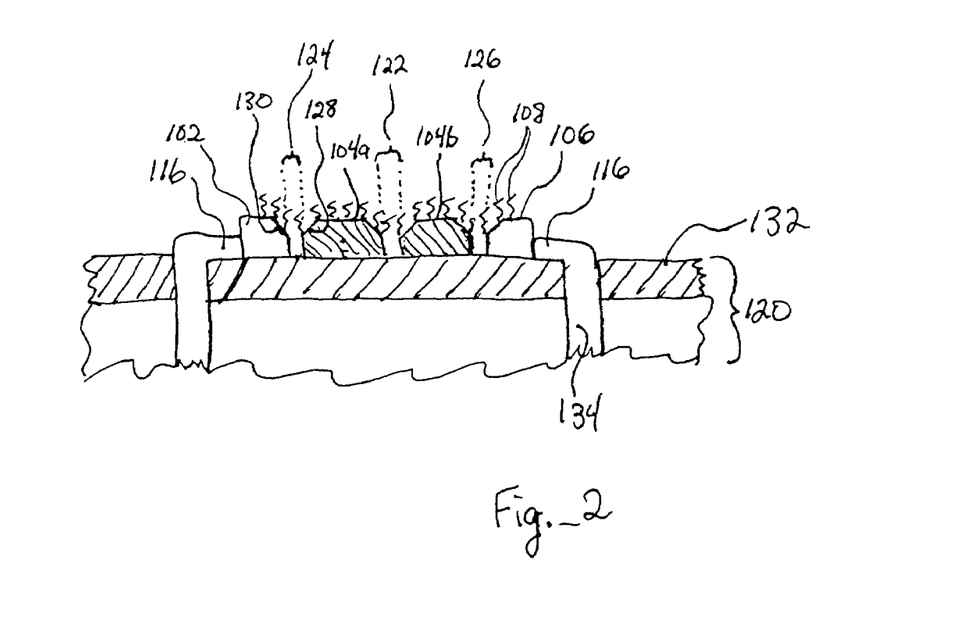
FIG. 2 depicts a feature of an embodiment of a microarray according to the present invention.

FIG. 2 illustrates an alternate embodiment of a single feature 100 of a microarray according to the present invention, and also illustrates several other features that may optionally be present. In FIG. 2, a substrate 120 includes a portion of non-conductive material in the form of a non-conductive layer 132. The non-conductive layer may be formed during manufacture as a layer of non-conductive material deposited on the underlying substrate, e.g. using integrated circuit manufacturing methods. In embodiments in which the composition of the substrate is a non-conductive material, the non-conductive layer is not distinguished from the substrate. A first electrode 102 is disposed on the substrate 120. A pad 104 of resistive material is disposed on the substrate 120 adjacent the first electrode 102, and a second electrode 106 is disposed on the substrate 120 adjacent the pad 104. In FIG. 2, the non-conductive layer 132 of the substrate 120 is the portion of the substrate 120 on which the pad 104 and first and second electrodes 102, 106 are disposed. The probe 108 is supported on the pad 104, and optionally may be supported on all or a portion of the first and/or second electrodes 102, 106, as well. In particular embodiments, one or more conductive traces 116 may be disposed on the substrate 120 electrically connecting each electrode to circuitry located on the substrate and/or off the substrate. Such circuitry may provide for interrogating the feature and/or for addressing the feature. As used herein, when circuitry is referred to as "on" the substrate, this should be interpreted to include circuitry which is physically located within the substrate on which the microarray features are supported. The conductive traces 116 provide for electrical communication between the electrodes 102, 106 and measurement apparatus during use of the microarray. Such measurement apparatus is used in interrogating the microarray. The electrodes may communicate to said measurement apparatus by means of vias 134 connecting the conductive traces 116 (if present) to the measurement apparatus.

Still referring to FIG. 2, the pad 104 is segmented, having a plurality of segments 104a, 104b separated by a fissure 122. In certain embodiments, the pad will typically have more than about 10, or more typically up to about 20, still more typically up to about 100, yet more typically up to about 600 or more segments, and will typically have at least one, more typically at least about 2, still more typically at least about 3, or yet still more typically at least about 5 segments The fissure 122 may extend all the way through the pad 104 (as illustrated in FIG. 2), or, in alternate embodiments, the fissure 122 may extend only partially through the pad 104 of resistive material, leaving a reduced thickness of resistive material disposed between the segments 104a, 104b of the pad 104. Thus the pad 104 may comprise a plurality of segments 104a, 104b which are separated from each other by fissures 122; in other words, the pad 104 may optionally define one or more fissures 122 defining segments 104a, 104b of the pad. The edge 128 of the segments of the pad nearest the fissure may have a rounded or angled (illustrated in FIG. 2) cross-section such that the fissure is wider at the "top" (distal from the substrate) than it is at the substrate surface. Alternatively, the fissure may extend perpendicularly from the surface of the substrate and be essentially the same width at both the "top" (distal to the substrate) and "bottom" (proximal to the substrate) of the fissure. In another alternative, the fissure may be narrower at the "top" (distal to the substrate) than at the "bottom" (proximal to the substrate) of the fissure. The width of the bottom of the fissure (the distance between the segments of the pad) may be any suitable distance at which the embodiment is still functional, such as at least about 50 nanometers wide, typically at least about 100 nanometers wide, more typically at least about 200 nanometers wide, still more typically at least about 300 nanometers wide, and up to about 10 micrometers wide or more, typically up to about 5 micrometers wide, more typically up to about 2 micrometers wide, still more typically up to about 1 micrometer wide.

In the embodiment of FIG. 2, a first gap 124 is defined between the first electrode 102 and the pad 104. A second gap 126 is defined between the second electrode 106 and the pad 104. The first gap and/or second gap, when present, generally extends the entire distance adjacent the electrode and the pad and separating the electrode and the pad. The electrode edge 130 nearest the pad may have a rounded or angled (illustrated in FIG. 2) cross-section such that the gap is wider at the "top" (distal from the substrate) than it is at the substrate surface. Alternatively, the gap may extend perpendicularly from the surface of the substrate and be essentially the same width at both the "top" (distal to the substrate) and "bottom" (proximal to the substrate) of the gap. In another alternative, the gap may be narrower at the "top" (distal to the substrate) than at the "bottom" (proximal to the substrate) of the gap. The width of the bottom of the gap (the distance between the electrode and the pad) may be any suitable distance at which the embodiment is still functional, such as at least about 50 nanometers wide, typically at least about 100 nanometers wide, more typically at least about 200 nanometers wide, still more typically at least about 300 nanometers wide, and up to about 10 micrometers wide or more, typically up to about 5 micrometers wide, more typically up to about 2 micrometers wide, still more typically up to about 1 micrometer wide.

In certain alternate embodiments, the gaps/fissures may be filled with another material whose resistance to the flow of electricity is different from that of the resistive material of the pad, such as a conductive material, a non-conductive material, or a different resistive material. In some embodiments, a feature comprises two different resistive pads having different composition and/or different resistance. The pad will typically have an essentially planar surface, but in alternate embodiments, the surface of the pad may be treated to have an increased surface area, for example to provide for increased binding of the probe 108. In other embodiments, the pad 104 of resistive material is optional, and in embodiments lacking the pad 104, the probe is supported on the substrate 120 at a position generally between the first electrode 102 and second electrode 106.

Figure 3:
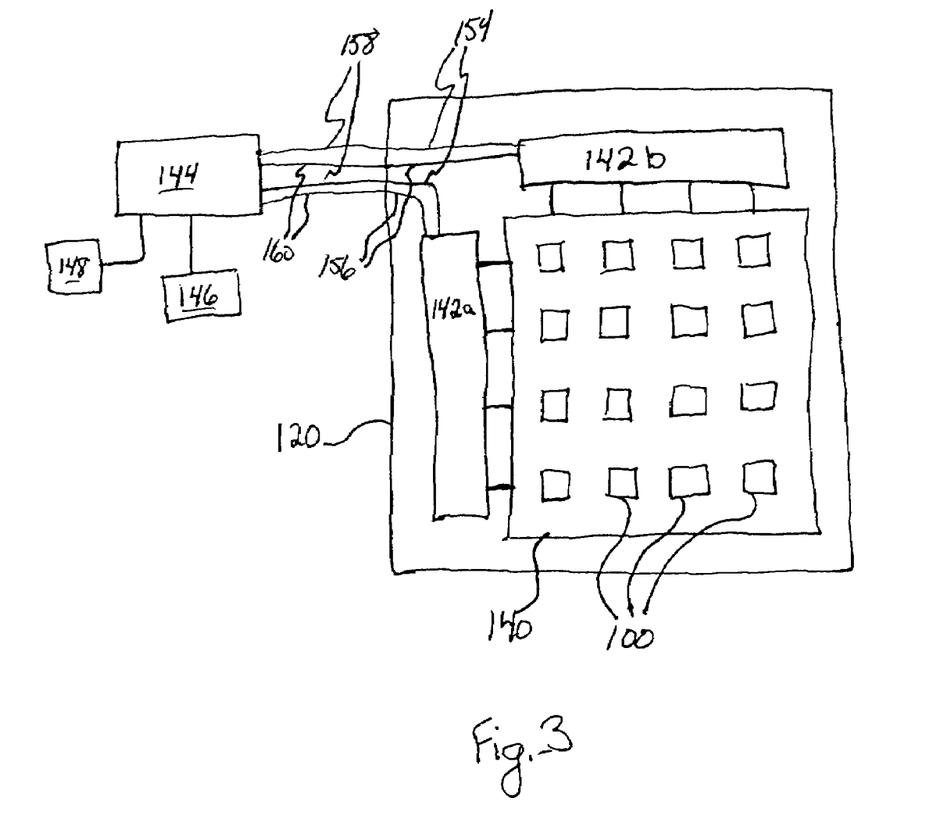
FIG. 3 shows an embodiment of an array of features according to the present invention disposed on a substrate.

The invention further provides for a microarray having a plurality of features such as that described with respect to FIG. 1 or 2 supported in an array format on a single substrate. FIG. 3 illustrates elements that may be included in a system for multiplexed analysis of a sample, the system incorporating such a microarray according to the present invention having integrated addressing circuitry. In FIG. 3, a plurality of features 100 (each feature 100 having a probe disposed between a first and second electrode, the probe optionally being supported on a pad of resistive material) such as that described above with respect to FIG. 1 or 2 are supported in an array format on a single substrate 120, thus forming an array of features 140. In the system illustrated in FIG. 3, circuitry 142a, 142b integrated on (and/or within) the substrate includes addressing circuitry for addressing the array of features 140; the circuitry 142a, 142b is in electrical communication with the features 100 on the array of features 140. To simplify interfacing to the array of features 140, the addressing circuitry may select one or more rows (circuitry 142a) and one or more columns (circuitry 142b) to interrogate individual features according to the present invention. In particular embodiments, the circuitry 142a, 142b includes circuitry for interrogation of the features. In some embodiments, each feature 100 of the array of features 140 includes circuitry operable to interrogate the feature 100, including optional data storage circuitry to store results of the interrogation; in such embodiments, the addressing circuitry operates to allow data to be read out from the data storage circuitry associated with each selected feature. Some embodiments may include other circuitry as necessary to perform the functions desired, e.g. functions of addressing and/or interrogating the features of the microarray and/or storing and retrieving data; such other circuitry may include amplifying circuitry, digital analog converters, analog digital converters, bridge circuitry, comparator circuitry, memory circuitry, and other circuitry known to those in the art, such circuitry being disposed in operable relation to the features of the microarray. In selected embodiments, the system for multiplexed analysis of a sample further includes integrated circuitry for accumulation and storage of data about each feature of the array of features. Such circuitry is disposed on (or within) the substrate and is operably associated with the electrodes of the features to receive data about one or more observable properties related to the state of one or more features of the array of features. In some embodiments the integrated circuitry for storage of data may include storage means in operable relation to the features of the array of features. The storage means typically stores numerical data (or data that is encoded as numerical data) obtained by analysis of the sample. The storage means may be similar to that known in the art such as, for example, D-type static flip-flops, a latch, a capacitor storing an analog value, and the like. The storage means may be a dynamic RAM replicator latch with a capacitor, which can store data but needs to be refreshed. In some embodiments, the storage means stores data about each feature 100 of the array of features 140, e.g. data such as identity of probe, value obtained from the measuring the observable property for each feature before and after the enhancement reaction, information about the sample, etc. The storage means may store an analog or digital value representative of a voltage, current, or other observable property, or may store a binary value representing a selected state, e.g. the fact a cell was selected.

The devices used in the present invention may be fabricated according to procedures well-known to those skilled in the art of digital and IC design and microarray fabrication, given the discosure herein. Reference books that are exemplary of those directed to the above include VLSI Technology by S. M. Sze (1988) ISBN 0-07-062735-5 and Basic VLSI Design by Pucknell and Eshraghian (1988) ISBN 0 7248 0105 7. Typical integrated circuits use two to five or more layers of interconnection metal with insulator layers in between. Modern IC's usually use an aluminum alloy for metallization in conjunction with "vias" of a tungsten alloy. The metal layers are generally of a thickness on the order of approximately about 0.1 to about 1 micron.

Continuing with reference to FIG. 3, the embodiment illustrated further include a microprocessor 144 operably associated with the features 100 on the substrate 120 via the circuitry 142a, 142b. The microprocessor 144 is in electrical communication with the circuitry 142a, 142b via address lines 154, 158 and data lines 156, 160. The address lines include on-substrate address lines 154 and external address lines 158. The data lines include on-substrate data lines 156 and external data lines 160. In certain embodiments, the circuitry on the substrate is in electrical communication with one or more externally accessible leads or contacts present on the substrate, and the leads or contacts are capable of communicating to remote circuitry or components, e.g. measurement apparatus or a microprocessor. In the embodiment shown, the microprocessor 144 is in electrical communication with a storage apparatus 146, such as a hard drive, tape drive, disk drive, RAM memory, flash memory, or other storage apparatus as are commonly known in the art. The microprocessor 144 is also operably associated with one or more input and/or output apparatus 148, such as a monitor, keyboard, mouse, or other such input and/or output apparatus as are commonly known in the art. In use, the microprocessor 144 is provided to control interrogation of the array of features 140, including supplying address signals to the addressing circuitry to control selection of features 100 and to receive signals (e.g. data from measuring observable properties of the features.).

The substrate 120 bearing an array 140 of features 100 (such as that shown in the system illustrated in FIG. 3) may contain a relatively small number of features 100 in an array 140, e.g. about 10 or more, about 20 or more, about 50 or more, about 100 or more. The substrate 120 may contain an array 140 of up to a large number of features 100, e.g. up to about 1000, up to about 5000, up to about 10,000, up to about 50,000, up to about 100,000, or even more. The size of the array of features may be varied depending on the desired application. Fewer or more features may be employed, depending on cost considerations, the size of the sample available for analysis and the size of the electrodes necessary to obtain the required sensitivity. Certain embodiments may include features that are designed to provide control or reference measurements in use of the microarray. For example, such a control feature may support a probe having a known identity that will bind with a standard moiety spiked into the sample at a known concentration. Alternative control or reference features known in the art may also be included.

The surface area of the substrate occupied by a single feature will typically be on the order of at least about 15 square microns and up to about 500 square microns or more for applications such as high density arrays; for arrays having a lower density of features on the array, the surface area occupied by a single feature may be up to about 1 square millimeter, or yet larger, depending on the application. Desirably, the array is a matrix of the order of 10,000 probe sites or more in an area several millimeters to several centimeters on a side.

Again referring to FIG. 3, each feature 100 includes a probe, e.g. a DNA or RNA probe. The probe at each feature is capable of binding to a known target, e.g. DNA. Typically, each feature 100 bears a different identity probe relative to other features on the substrate, though there may be duplicate probes present on the array 140. The identity of probes may be selected according to the desired target to be assayed; such selection is within the capability of those skilled in the art. Oligonucleotides, single or double stranded DNA or RNA, antibodies, peptides and other probes known to those skilled in the art may be used.

During use of the microarray, measurement circuitry is in operable relation to the addressing circuitry and the features of the array. The measurement circuitry may form a part of the substrate or may be located external to the substrate. In particular embodiments, the measurement circuitry controls the voltage at one of the first electrode and the second electrode with respect to the other electrode or with respect to some other reference point. The measurement circuitry may additionally or alternatively may control the current in one of the electrodes. When one aspect is set, the other may be monitored via the measurement circuitry. For example, when the voltage is set, the current may be monitored. The voltage and/or current may be applied in a direct current mode or may vary with time. The voltage applied is typically less than about 100 volts, more typically less than about 20 volts, and typically greater than about 1 millivolt, more typically greater than about 20 millivolts. The measurement circuitry is typically controlled by a microprocessor during use of the microarray.

Gold may be employed for the conductive elements (e.g. conductive traces) or electrodes. For cost reasons in the present invention aluminum may be employed for connecting circuitry, e.g. forming conductive traces. Fixed electrodes may be plated over using well-known fabrication processes, with a variety of metals, including gold and nickel, chosen to be the most compatible with the attachment chemistry for the probe. In addition to aluminum, suitable metals include gold, tin, platinum, palladium, and various metal combinations.

In some embodiments, the substrate comprises a non-conductive material in the form of a non-conductive layer supporting the features (i.e. the first electrode, the second electrode, and the probe disposed between the first electrode and the second electrode), and the substrate further comprises a conductive layer underlying the non-conductive layer. The nonconductive layer separates each device from the underlying conductive layer of the substrate, which serves as a common bus electrically connecting to a first electrode of each device (e.g. forming a common ground), typically by means of vias extending through the non-conductive layer. The non-conductive layer may also serve to separate the conductive layer from conditions used in exposing the probe to target, e.g. solutions containing target, or from conditions used during the enhancement reaction. The non-conductive layer may be a thin film in the range of about 0.1 to about 5 microns thick, such as in the range of about 0.2 to about 2 microns thick, and is made of an insulating (i.e. not allowing conduction of electrical current) material such as silicon dioxide and the like. The non-conductive layer may be selected to be resistant to chemicals encountered while assaying a sample. The non-conductive layer may be formed on and intrinsically adhered to a portion of the substrate during the manufacturing process. The non-conductive layer may be conveniently applied by deposition techniques, e.g., plasma enhanced chemical vapor deposition, photomasking methods, or the like.

The electrodes of the features disposed on the substrate are typically in electrical communication with the circuitry on (or within) the substrate by means of conductive elements such as are known in the art, e.g. conductive traces, metal vias extending through a non-conductive layer of the substrate, or an underlying conductive layer of the substrate serving as a bus. See, for example, the depiction of via 132 in FIG. 2. These holes are typically on the order of fractions of microns, usually about 0.2 to about 2 microns in diameter and may be formed by microlithographic or other techniques well-known in the art of semiconductor manufacturing such as electron beam lithography, ion beam lithography, or molecular beam epitaxy.

In particular embodiments, each feature of the microarray includes a pad of resistive material disposed on the substrate between the first electrode and the second electrode, and the probes are supported on the pad. The pad of resistive material may comprise any resistive material that is suitably inert to the conditions of use and/or manufacture of the device. For example, the resistive material should be selected to be inert to the conditions used to bind the probe to the pad and also to the conditions for binding the target to the probe. Such conditions may include a range of solutions including aqueous and organic solvents and mixtures thereof, various solutes typically encountered during use of the device, and a range of pH (typically from pH 4 to pH 10, more typically from pH 2 to pH 12). The pad should be inert to the range of temperatures to which the device is exposed, such as over the temperature range of about minus 20 degrees Celsius to about 200 degrees Celsius, or typically about minus 10 degrees Celsius to about 100 degrees Celsius. Since the pad is a resistive material and the substrate typically comprises a non-conductive material, the pad typically has a different composition compared to the substrate (if present).

The pad will typically comprise materials such as are commonly used in thin-film resistive component applications, such as carbon thin films, metal thin films, metal nitride, nichrom (NiCr), tantalum nitride ($Ta_2N$), silicon chrome, metal oxide (such as tin oxide) and others known to those of skill in the art. The pad typically will cover an area on the surface of the substrate of at least about 15 square microns and up to about 1500 square microns or more (for applications such as high density arrays); however, for arrays having a lower density of devices on the array, the surface area of a pad may be up to about 1 square millimeter, or yet larger, depending on the application. In some embodiments, the thickness of the pad is at least about 10 nanometers, or at least about 25 nanometers, and may be up to about 250 nanometers, or up to about 400 nanometers, or even more, depending on design considerations including the composition of the resistive material of the pad. In particular embodiments, the pad includes layers of materials formed via thin film vapor deposition in a vacuum chamber using evaporation and sputtering processes. Such processes can be used, for example, to deposit a thin layer of metal by vacuum deposition, plasma enhanced chemical vapor deposition or other means onto a substrate material.

The pad is typically a thin film, the thin film having an obverse face supporting the probe, a reverse face supported on the substrate, and an edge at the perimeter of the thin film. The first and second electrodes generally are disposed adjacent the edge. In particular embodiments the first and second electrodes do not extend over (or under) a significant portion of the obverse face of the thin film (typically less than about 5%). Depending on the construction of certain embodiments, the first electrode and/or second electrode may overlap a small portion (typically less than 5%) of the obverse surface of the thin film, or a small portion of the thin film may overlap the first and/or second electrode, the edge of the thin film may closely abut (and contact) the first and/or second electrode, or the edge of the thin film and an adjacent first and/or second electrode may define a gap separating the pad and the electrode. Other possible configurations should be apparent to those skilled in the art and should be considered to be part of the scope of the invention.

In particular embodiments having a first electrode directly joined to a pad of resistive material, a second electrode directly joined to the pad of resistive material, and wherein the pad is a single pad (i.e. is a single segment), the measured resistance between the first electrode and the second electrode is less than about 10 megohms, such as less than about 5 megohms, less than about 2 megohms, less than about 1 megohm, less than about 0.5 megohms, less than about 0.2 megohms, or less than about 0.1 megohms. In certain such embodiments, the measured resistance is at least about 0.1 kilohms, such as at least about 0.2 kilohms, at least about 0.5 kilohms, at least about 1 kilohm, at least about 2 kilohms, at least about 5 kilohms, at least about 10 kilohms, or at least about 50 kilohms. In some such embodiments, the first electrode, the second electrode, and the pad may optionally be disposed on a non-conductive substrate. The above-referred to measurement of resistance should be measured on a device having probe supported on the pad, but before any hybridization reaction or enhancement reaction has been done. The resistance measurement is made by first drying the device and then measuring with a suitable ohmmeter.

Alternatively, in embodiments having one or more gaps and/or fissures (e.g. the first electrode is not directly joined to the pad) (further e.g. the pad of resistive material consists of a plurality of segments with fissures between the segments), the above-referenced measurement of resistance is not suitable due to the presence of one or more gap(s) and/or fissure (s). Certain embodiments having one or more gaps and/or fissures may be characterized via a test device which is similar to the given embodiment having the gap(s) and/or fissure (s) but which lacks the gap(s) and/or fissure(s). The first and second electrodes on the test device should have a similar configuration to the first and second electrodes of the given embodiment, i.e. the length, width, and height of the first and second electrodes on the test device should be within +/−30% of the embodiment. The pad of resistive material on the test device should be in electrical contact with the first and second electrodes (filling in the gaps and/or fissures) but otherwise have a similar configuration, i.e. the length, width, and height of the pad of resistive material on the test device should be within +/−30% of the given embodiment The measured resistance between the first and second electrodes of such a test device is less than about 10 megohms, such as less than about 5 megohms, less than about 2 megohms, less than about 1 megohm, less than about 0.5 megohms, less than about 0.2 megohms, or less than about 0.1 megohms. In certain such embodiments, the measured resistance between the first and second electrodes of the test device is at least about 0.1 kilohms, such as at least about 0.2 kilohms, at least about 0.5 kilohms, at least about 1 kilohm, at least about 2 kilohms, at least about 5 kilohms, at least about 10 kilohms, or at least about 50 kilohms. The resistance measurement is made by first drying the test device and then measuring with a suitable ohmmeter.

The probes are typically attached to a probe-bearing surface, wherein the probe-bearing surface is typically selected from a surface of the substrate available for binding to the probe or a surface of the pad of resistive material available for binding the probe. The probe may be attached to the probe-bearing surface directly or via intervening moieties, e.g. where the probe-bearing surface has been modified. In certain embodiments, the probe-bearing surface may be modified, e.g. to present desired chemical groups on the probe-bearing surface, or to modify physical characteristics of the probe-bearing surface, e.g. conductivity or hydrophilicity, or for other purposes, e.g. to enhance or control binding of probe. Such chemical groups may include chemical linkers such as alkenethiols, conducting polymers such as polypyrrole or polyaniline, organosilanes and dendrimers. Other surface modifications using conjugate pairs can also be used such as avidin-biotin or strepavidin-biotin or other chemical linkers with functional groups specific for amines (N-hydroxysuccimide) for example. Surface modifications may also include a thin layer of a gel matrix disposed on the surface of the pad. Certain bifunctional moieties may be used to modify the probe-bearing surface, e.g. bifunctional moieties having a first functionality that covalently binds to the probe-bearing surface and a second functionality that binds to a chemical linker that is attached to the probe.

A known procedure for the derivatization of a metal oxide surface uses an aminoalkyl silane derivative, e.g., trialkoxy 3-aminopropylsilane such as aminopropyltriethoxy silane (APS), 4-aminobutyltrimethoxysilane, 4-aminobutyltriethoxysilane, 2-aminoethyltriethoxysilane, and the like. APS reacts readily with the oxide and/or siloxyl groups on metal and silicon surfaces. APS provides primary amine groups that may be used as functional groups for attaching probes. Such a derivatization procedure is described in EP 0 173 356 B1. Methods of incorporating other organosilane coupling agents to functionalize the pad surface are described in, e.g., Arkins, Silane Coupling Agent Chemistry, Petrarch Systems Register and Review, Eds. Anderson et al. (1987) and U.S. Pat. No. 6,258,454. A surface optimized for in-situ synthesis of DNA arrays is described in U.S. Pat. No. 6,258,454. Other methods for treating the surface will be apparent to those skilled in the art in view of the teaching herein.

The substrate comprises any suitably non-conductive material. The substrate typically comprises a material that is suitably inert to the conditions of use and/or manufacture of the device. For example, the substrate should be designed to be suitable for use under conditions used to form the pad on the substrate and also to the conditions for performing analysis on samples containing target. Such conditions may include a range of solutions including aqueous and organic solvents and mixtures thereof, various solutes typically encountered during use of the device, and a range of pH (typically from pH 4 to pH 10, more typically from pH 2 to pH 12). The substrate should be inert to the range of temperatures to which the device is exposed, such as over the temperature range of about minus 20 degrees Celsius to about 200 degrees Celsius, or typically about minus 10 degrees Celsius to about 100 degrees Celsius. Even broader temperature ranges may be encountered under certain processes used in the manufacture of the device, and the substrate material should be chosen to be compatible with such techniques where necessary.

In some embodiments the substrate comprises a portion of non-conductive material (e.g. that portion on which the pad and electrodes are disposed), while other portions of the substrate may include other materials, including conductive materials, such as conductive elements and/or doped semiconductor materials; in particular embodiments the substrate comprises an integrated circuit on a semiconductor chip. In a typical embodiment, the portion of the substrate on which a feature is disposed will be non-conductive, and may be a non-conductive layer added onto the rest of the substrate during the process of manufacture of the substrate. Materials typically suitable for use in substrates include semiconductors and materials typically used in semiconductor packaging as well as other materials having the properties indicated herein.

The device may be formed by any suitable means of manufacture, including semiconductor manufacturing methods, microforming processes, molding methods, material deposition methods, LIGA processes, etc., or any suitable combination of such methods. In certain embodiments one or more of the electrodes and/or the pad may be formed via semiconductor manufacturing methods on a semiconductor substrate. Thin film inorganic coatings may be selectively deposited on portions of the substrate and/or pad surface. Examples of suitable deposition techniques include vacuum sputtering, electron beam deposition, solution deposition, and chemical vapor deposition. The inorganic coatings may perform a variety of functions. For example, the coatings may be used to increase the hydrophilicity of a surface or to improve high temperature properties. Conductive coatings may be used to form electrodes. Coatings may be used to provide a physical barrier on the surface, e.g. to retain fluid at specific sites on the surface. The devices used in the present invention may be fabricated according to procedures well-known in the arts of microarray and semiconductor device manufacturing.

In some embodiments the probes may be selected from biomolecules, such as polypeptides, polynucleotides, glycoproteins, polysaccharides, hormones, growth factors, peptidoglycans, or the like. The probe typically is comprised of natural nucleotides such as ribonucleotides and deoxyribonucleotides and their derivatives although unnatural nucleotide mimetics such as 2'-modified nucleosides, peptide nucleic acids and oligomeric nucleoside phosphonates are also used. In embodiments employing oligonucleotide probes, the probes may be synthesized, in situ, on the surface of the substrate (or on the surface of the pad, if present) in either the 3' to 5' or 5' to 3' direction using the 3'-β-cyanoethyl-phosphoramidites or 5'-β-cyanoethyl-phosphoramidites and related chemistries known in the art. In situ synthesis of the oligonucleotides may also be performed in the 5' to 3' direction using nucleotide coupling chemistries that utilize 3'-photoremovable protecting groups (U.S. Pat. No. 5,908,926). Alternatively, the oligonucleotide probes may be synthesized on the standard controlled pore glass (CPG) in the more conventional 3' to 5' direction using the standard 3'-β-cyanoethyl-phosphoramidites and related chemistries (Caruthers M. et al., *Method Enzymol.*, 154; 287-313 (1987), and U.S. Pat. Nos. 4,415,732 and 4,458,066) and incorporating a primary amine or thiol functional group onto the 5' terminus of the oligonucleotide (Sproat et al., *Nucleic Acids Res,* 1987, 15, 4837, and Connolly and Rider, *Nucleic Acids Res;* 1985, 13, 4485). The oligonucleotides may then be covalently attached to the probe-bearing surface of the substrate (or the pad surface) via their 5' termini using thiol or amine-dependent coupling chemistries known in the art. The density of the probes on the surface can range from about 1,000 to 200,000 probe molecules per square micron. The probe density can be controlled by adjusting the density of the reactive groups on the surface of the pad for either the in situ synthesis or post-synthesis deposition methods. Other suitable means for synthesis of probe as are known in the art may be employed.

Typically, oligonucleotide probes are comprised of, but not limited to, the four natural deoxyribonucleotides; deoxythymidylic acid, deoxycytidylic acid, deoxyadenylic acid and deoxyguanylic acid. The probes can also be comprised of the ribonucleotides, uridylic acid, cytidylic acid, adenylic acid, and guanylic acid. Modified nucleosides may also be incorporated into the oligonucleotide probes. These include but are not limited to; 2'-deoxy-5-methylcytidine, 2'-deoxy-5-fluorocytidine, 2'-deoxy-5-iodocytidine, 2'-deoxy-5-fluorouridine, 2'-deoxy-5-iodo-uridine, 2'-O-methyl-5-fluorouridine, 2'-deoxy-5-iodouridine, 2'-deoxy-5(1-propynyl) uridine, 2'-O-methyl-5(1-propynyl)uridine, 2-thiothymidine, 4-thiothymidine, 2'-deoxy-5(1-propynyl)cytidine, 2'-O-methyl-5(1-propynyl)cytidine, 2'-O-methyladenosine, 2'-deoxy-2,6-diaminopurine, 2'-O-methyl-2,6-diaminopurine, 2'-deoxy-7-deazadenosine, 2'-deoxy-6methyladenosine, 2'-deoxy-8-oxoadenosine, 2'-O-methylguanosine, 2'-deoxy-7-deazaguanosine, 2'-deoxy-8-oxoguanosine, 2'-deoxyinosine or the like.

Typically, the oligonucleotide probes can range in length from, but not limited to a range of about 5 to about 100 nucleotides, such as about 8 to about 80 nucleotides, such as about 10 to about 60 nucleotides, and such as about 15 to about 50 nucleotides. Longer oligonucleotide probes are typically employed in applications where the sample contains a high sequence-complexity target mixture. Shorter oligonucleotide probes are typically employed in applications where single nucleotide discrimination, such as mutation detection, is important.

The probe provides a device that is specific and complementary to a particular target, e.g. a specific nucleic acid sequence. For example, a probe may be complementary to a specific target. In an embodiment, probes that bind to single or multiple mutations of a given target (or to an otherwise modified target) may be presented on the array.

In embodiments in which the target is a nucleic acid, the target nucleic acid may be genomic DNA, genomic RNA, messenger RNA, ribosomal RNA or transfer RNA, an oligonucleotide or polynucleotide of DNA or RNA generated by enzymatic process such as PCR or reverse transcription, or any synthetic DNA, RNA, or any other desired nucleic acid or any combination thereof. The target nucleic acid may be double stranded or single stranded. It is preferred that the target be single stranded in order to increase the efficiency of its interaction with the probe sequences. To this end, the target may contain modified nucleotides for the purposes of reducing secondary structure by disrupting intramolecular base-pairing interactions or increasing the stability of the probe-target interaction.

The architecture of the array probes may be either generic or specific with regard to the complementary target sequences that it may hybridize with. For example, an array of all possible 16,384 7-mer probe sequences could be used to interrogate targets having any sequence. The advantage of such an array is that it is not application specific and therefore generic. Alternatively, the probe array may contain oligonucleotide probe sequences that are complementary to a specific target sequence or set of target sequences and individual or multiple mutations thereof. Such an array is useful in the diagnosis of specific disorders, which are characterized by the presence of a particular nucleic acid sequence. For example, the target sequence may be that of a particular exogenous disease causing agent, e.g. human immunodeficiency virus, or alternatively the target sequence may be that portion of the human genome which is known to be mutated in instances of a particular disorder, e.g. sickle cell anemia or cystic fibrosis, or to a portion of a genome known to be associated with certain phenotypes, e.g. resistance to certain drugs, over-reactivity to certain drugs, or even susceptibility to side-effects of certain drugs.

In the art, the detection of nucleic acid sequences by hybridization procedures is typically carried out using oligonucleotide probes between 12 and 25 nucleotides in length. Probes of this length are generally utilized to increase the specificity of the probe-target interaction when using high sequence-complexity target mixtures and to stabilize the probe-target interaction. In the present invention, the probes can be between about 5 and about 100 nucleotides in length depending upon the detection mode employed. The use of shorter probes (e.g. 6-mers, 7-mers, and 8-mers) allows for a sequence-complete set of probes to be incorporated into a single array consisting of about 65,000 or fewer features, each possessing a defined sequence. For example, an array of all 6-mer sequences would consist of 4,096 features each possessing a unique sequence. An array of all 7-mer sequences would consist of 16,384 features and an array of all 8-mers would consist of 65,536 features. Although the use of shorter probes results in a reduced overall stability of probe-target interaction, they are better for interrogating single nucleotide changes in the target sequence.

Detection of Targets

The microarray according to the present invention is intended for use in a molecular recognition-based assay for the analysis of a sample suspected of containing one or more target molecules or moieties such as specific nucleic acid sequences. The probes of the array are provided for the purpose of binding and detecting specific target nucleic acid sequences. The hybridization between the probe and target nucleic acid sequences may occur through the standard Watson-Crick hydrogen-bonding interactions or other known specific binding interactions known in the art. Specifically contemplated are schemes allowing for reduced secondary structure in probes and/or target molecules, such as those disclosed in U.S. patent application Ser. No. 10/324,409 entitled "Method Of Producing Nucleic Acid Molecules With Reduced Secondary Structure", filed on Dec. 18, 2002, and also those described in U.S. patent application Ser. No. 09/358,141 entitled "Method Of Producing Nucleic Acid Molecules With Reduced Secondary Structure", filed on Jul. 20, 1999.

In one approach, cell matter is lysed, to release its DNA as fragments or other targets of interest, which are then separated out by electrophoresis or other means well known in the art, and then optionally tagged with a linker molecule or a label. The resulting mixture containing the targets (e.g. DNA fragments) is exposed to an array of features (e.g. displaying an array of oligonucleotide probes), whereupon selective attachment to corresponding probe sites takes place. The array is then washed and further processed to reveal for analysis and interpretation the sites where attachment occurred. The further processing steps may include binding a label to the optional linker molecule. The label may potentially be bound to the target prior to the binding of the target to the probe, or, alternatively, the label may be bound to the target after the binding of the target to the probe.

In operation, the sample is brought into contact with a microarray as described herein by means of any system conventional in the art, such as by means of pipettes, tubing, or placing the microarrray in a well or other fluid containment structure along with the sample. In an embodiment, a fluid containment structure is a sealed container fabricated from an inert material such as plastic, creating a sample chamber where the target can contact every probe on the microarray. The chamber volume should be sized to closely fit the microarray to reduce the amount of sample needed for the analysis.

The label is any moiety leading to a change in observable characteristic upon enhancement such that the change in observable characteristic may be measured between the electrodes of a feature on a microarray. The label is typically any moiety that allows metal or another electrically conductive material to be preferentially deposited in the region between the electrodes of the feature. The label may act as a localized catalyst for metal deposition. In typical embodiments, the label is a metal nanoparticle, typically a gold (or silver) nanoparticle having a diameter in the nanometer range, e.g. from about 0.7 nanometers to about 5 nanometers, typically in the range from about 1 nm to about 2 nm. After the label is bound to the probe, an enhancement reaction is applied to result in deposition of metal (or another electrically conductive material) in the region between the electrodes of the feature. The metal, which has a high conductivity, alters an observable property of the feature, e.g. an electrical property such as resistance, impedance, conductance, capacitance, current, potential, transmission of a signal between the two electrodes or other electrical property. The label is typically a metal nanoparticle, e.g a gold nanoparticle or a silver nanoparticle.

The attachment of the label may occur via any suitable method and at any suitable step in the process that does not interfere with the overall method. In some embodiments, the label may be attached directly to the target prior to binding of the target by the probe. In other embodiments, the label may be attached after the binding of the target by the probe. Methods of attaching the label are well known in the art pertaining to the use of such labels. In certain embodiments, a conjugate binding pair is used to attach the label to the target, or in some cases, to the probe. In cases in which the label, e.g. the gold nanoparticle, is attached via a conjugate binding pair, e.g. biotin-avidin, the individual members of the conjugate binding pair may be attached using any suitable method and at any suitable step in the process that does not interfere with the overall method. Methods of attaching the members of the conjugate binding pair to, e.g. the label, the target, and/or the probe, are well known in the art pertaining to the use of such conjugate binding pairs. A reaction may then be performed in which the separate molecules incorporating the complementary members of the conjugate binding pair are brought into proximity and allowed to bind to each other. Consistent with the methods described herein the label may be incorporated into the target prior to bringing the features of a microarray in accordance with the present invention into proximity with a sample suspected of containing the target molecule. Alternatively, the label may be incorporated into the target subsequent to bringing the features of a microarray in accordance with the present invention into proximity with a sample suspected of containing the target molecule.

Typically, the target is a polynucleotide, and the label or linker moiety (e.g. a member of a conjugate binding pair) can be attached to the target at any nucleotide position via the nucleotide base, ribose ring or phosphate backbone. In some embodiments, the label or linker moiety is attached to either the 3' or 5' terminal nucleotide of the target. In another embodiment, the target is associated with one member of a conjugate binding pair, and the label is associated with the other member of the conjugate binding pair, such that the label may be attached to the target via the conjugate binding pair. Examples of suitable high affinity conjugate binding pairs are the biotin-streptavidin pair and the digoxigenin-antidigoxigenin pair (Kessler, Advances in Mutagenesis, Berlin/Heidelber; Springer-Verlag; 105-152 (1990)). As an example, a polynucleotide target may have a biotin moiety attached (e.g. via the C5 position of pyrimidines or the C8 position of purines), and the label (e.g. gold nanoparticle or silver nanoparticle) may be conjugated to a streptavidin molecule. The conjugate binding pair serves as a means of linking the label to the target. Similarly, in an example using the digoxigenin-antidigoxigenin pair, the digoxigenin hapten moiety would be attached to a polynucleotide target and the label would be associated with the antidigoxigenin.

Measurement of the Observable Property

Target molecules in the sample specifically bind to the probe. This binding is detected by means of a label incorporated into or otherwise associated with the target, e.g. via an intermediate binding or enhancement process.

"Enhancement", as used herein, refers to a process of contacting the label with a reagent wherein the reagent modifies the label to produce or alter the observable property, indicating the presence of the label. An enhancement reaction is any such reaction that modifies the label to result in the change in observable property of the device to which the target is bound. In a typical embodiment, the enhancement reaction results in conductive material, e.g. metal, being deposited in the region of the probe, thereby changing an electrical characteristic of the device. The enhancement reaction typically comprises applying an enhancement reagent to the label bound to the immobilized probe on the surface of the pad. In some embodiments, the enhancement reaction includes: (a) contacting a label disposed between a first electrode and a second electrode of a feature with a source of metal ions to result in metal deposited between the first electrode and second electrode, and (b) removing the source of the metal ions after metal has been deposited between the first electrode and second electrode. Typically, the enhancement reaction is performed simultaneously at a plurality of features of a microarray by contacting the microarray surface with the enhancement reagent (e.g. the source of metal ions). After removing the enhancement reagent, the microarray surface is typically rinsed and dried to remove excess reagents from the site of the first electrode and second electrode. The observable property is measured after the enhancement, typically after the rinsing and drying.

In a typical embodiment, binding of the probe by the target is typically detected by enhancement of a label comprising a metal nanoparticle, e.g. a gold nanoparticle or silver nanoparticle. In a typical enhancement reaction, the metal nanoparticle is contacted with an enhancement reagent comprising a solution of gold chloride. The metal nanoparticle label nucleates the deposition of gold metal from the AuCl solution, thus increasing the diameter of, e.g. a 1.4 nm gold nanoparticle, to sizes ranging from 2-20 nm or up to 50 nm or more in diameter. Where the label comprises a gold nanoparticle, a typical enhancement reagent comprises a solution of AuCl in the presence of a catalyst and an initiator. Gold nanoparticles and enhancement reagent solutions are known in the art and may be obtained from, e.g. Nanoprobes, Inc (Yaphank, N.Y.). In an embodiment, the enhancement reaction is conducted as follows: Strep-avidin gold nanoparticles are contacted with a device (e.g. an array of features) on which biotin-labeled target is immobilized. The device (e.g. an array of features) is incubated for 30 minutes then washed extensively for 10 minutes in PBS to result in gold nanoparticles being selectively bound to the features of the microarray via the biotin/strep-avidin linkage. The enhancement kit, as purchased from the commercial supplier noted above, has four reagents. Reagent A is an enhancement reagent; reagent B is an activator; reagent C is an initiator; and reagent D is buffer. Equal volumes of reagent A and B are combined then followed by equal volume of C followed by reagent D, according to the directions supplied by the supplier. The gold nanoparticles nucleate deposition of gold metal resulting in nanoparticles that have diameters up to about 50 nm or more. Alternate enhancement reagents include the use of silver enhancer solution which is composed of $AgNO_3$ and hydroquinone. The silver enhancer typically needs to be replaced every 2 or 3 minutes to avoid formation of silver particulate in solution.

The label is detected (via the electrodes at each feature) by consequent change in an observable property. The observable property may be, e.g the resistance measured across the two electrodes, or other suitable measurable observable property, such as conductance, capacitance, impedance, current, potential, transmission of a signal between the two electrodes, or the like. The observable property may be measured as an absolute quantity or as a quantity relative to some other element, such as a reference, that may be present on the device or external to the device. A calculation or comparison may be applied to the measured observable property to derive further information from the measured property. For example, the measured observable property from a given feature may be compared against a standard curve. Establishing the standard curve is within ordinary skill in the art given the disclosure herein.

The change in the observable property of the device may be measured using measurement apparatus operably associated with the feature or array of features. In some embodiments, such measurement apparatus may be located "off-substrate", that is not physically part of the substrate, but which measurement apparatus is electrically coupled with the feature or array of features on the substrate. In typical embodiments, the array of features is supported on an array substrate which includes an integrated circuit, wherein each feature is as described earlier herein, and the integrated circuit includes addressing circuitry in operable relation to features of the array of features. In such embodiments an address signal is provided via one or more address lines to the addressing circuitry to select one or more features at which the observable property is to be measured. The selected feature is then interrogated by the measurement apparatus, and the measurement apparatus receives a signal corresponding to the value of the observable property from the microarray via one or more data lines. The address lines and the data lines may be in electrical communication with an interface of a microprocessor used to control the system.

Various electronic signal detection methods known in the art, such as potentiometry and amperometry, can be employed with the device according to the present invention. In particular embodiments, the first and second electrodes of a given device are in electrical communication with measurement apparatus that controls and monitors the relevant parameters such as voltage, current or capacitance to measure the observable property. In certain embodiments incorporating an array of features, the array of features is a single use, disposable item that interfaces to a measurement apparatus that is an instrument designed for repeated use; the measurement apparatus controls and monitors the relevant parameters and is capable of interrogating each feature individually or in combination with one or more other features on the substrate.

In an embodiment the first electrode is electrically coupled to the second electrode via a pad of resistive material. After the binding of the target to the probe on the pad, the enhancement reaction results in deposition of metal adjacent the pad such that an observable property of the device is altered (i.e. the coupling between the two electrodes is modified). The altered observable property indicates binding of the target to the probe. The observable property is typically an electrical property measured by accessing an electrode of the device; suitable electrical properties include resistance, impedance, capacitance, transmission of a signal between the electrodes, or the like.

In some embodiments the measured observable property may be compared to measurements taken before the enhancement reaction is applied. In some embodiments measurements of an observable property are made on a reference or control device on the array and the results compared with the measured observable property of one of the devices on the array.

Appropriate washing steps may be included throughout the process, for example for a time and under conditions sufficient to remove excess reactants. The wash solution may be buffered at a pH between 4 and 12 and contain sufficient mono and divalent salts to remove the reaction components from the surface of the array. It is preferred that the wash solution contain some detergent such as sodium dodecylsulfate (SDS), Triton X-100 or the like. Small amounts of organic solvents such as acetonitrile may also be added in order to disrupt any non-specific hydrophobic binding of the target and nucleotide analogues to the array surface. Typically a typical washing step is performed with, e.g. a buffered solution containing 25 mM Tris-Cl (between pH 7-9), 150 mM NaCl, bovine serum albumin ranging from 0.01 to 0.15% and Tween® from 0.01 to 0.1% at 25° C. for 30 to 120 minutes.

Further Embodiments

One embodiment of the present invention is a method for detecting a target molecule using a microarray having a plurality of features supported on a substrate, wherein the substrate comprises an integrated addressing circuitry in operable relation to each of the plurality of features. Each feature comprises a first electrode disposed on the substrate, a second electrode disposed on the substrate a distance from the first electrode, and a probe disposed between the first electrode and second electrode. In typical embodiments, the distance between the first electrode and second electrode of a given feature is typically at least about 0.1 micrometers, more typically at least about 0.5 micrometers, still more typically at least about 1 micrometers, yet more typically at least about 2.5 micrometers, yet still more typically at least about 5 micrometers; and is typically less than about 10 micrometers, more typically less than about 25 micrometers, still more typically less than about 50 micrometers, yet more typically less than about 100 micrometers. In some embodiments, the distance between the first electrode and second electrode of a given feature is defined by the size of the pad of resistive material (including any gaps and/or fissures) disposed between the first and second electrode. In certain embodiments, each feature includes a pad of resistive material disposed between the first electrode and second electrode, and the probe corresponding to the feature is supported on the pad. In the method for detecting a target molecule, the microarray is contacted with a sample suspected of containing the target molecule. The target molecule is labeled with a label, and an enhancement reaction is applied to the label to alter an observable property at one or more features of the microarray. The enhancement reaction typically includes contacting the label with an enhancement reagent (e.g. a source of metal ions) to result in deposition of metal at the label, and removing the enhancement reagent from the label prior to interrogation of the feature. An address signal is delivered to the addressing circuitry to select a feature to be interrogated. The feature is then interrogated by accessing at least one of the electrodes of the selected feature to measure the observable property. Any observable property that can be used to establish a correlation between the binding of the probe by the target and the observable property may be used, such as, e.g. an electrical property such as resistance, impedance, capacitance, transmission of a signal, or the like. The magnitude of the corresponding changes indicates the presence or absence of the target molecule in the sample. Typically, each feature of the microarray may be selectively addressed to detect, by means of the electrodes of each feature, corresponding changes in the observable property produced as a result of the presence of labeled and enhanced target bound to the probe adjacent the electrodes. Each device of the array may have a different probe, thus enabling a plurality of different targets to be analyzed on a single array. In an embodiment, the corresponding changes of the observable property may be mapped against the concentration of the target in a set of standard solutions to develop a standard curve to derive information about concentration of target in a sample solution. Such mapping of concentration may be readily performed by one of skill in the art given the disclosure herein.

Each device of the array may have a different probe supported on the pad, thus enabling a plurality of different targets to be analyzed on a single array in a multiplex assay. In typical embodiments, binding can be detected by labeling the target, allowing the target to hybridize to a surface-bound probe, washing away the unbound target, enhancing the label, and detecting the enhanced, labeled target that remains by measuring an observable via the electrodes. In another approach, a "sandwich" is formed comprised of the probe bound to the pad, the target, and a second probe which also binds to the target and which is labeled. In the "sandwich" approach, the (unlabeled) target is allowed to hybridize to a surface-bound probe, unbound target is washed away, and the target bound to the probe is then contacted with a labeled probe that binds to the target. After rinsing excess labeled probe off, the label is enhanced, and the enhanced, labeled target is detected by measuring an observable via the electrodes.

EXAMPLES

The practice of the present invention will employ, unless otherwise indicated, conventional techniques of synthetic organic chemistry, biochemistry, molecular biology, and the like, which are within the skill of the art. Such techniques are explained fully in the literature.

The following examples are put forth so as to provide those of ordinary skill in the art with a complete disclosure and description of how to perform the methods and use the apparatus disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric. Standard temperature and pressure are defined as 20° C. and 1 atmosphere.

An example of a protocol used to attach probes to the resistive pad and the subsequent hybridization of target labeled with biotin and the binding of strepavidin-gold and its enhancement is described.

A wafer comprising a substrate having an array of electrode pairs disposed thereupon is obtained, wherein each electrode pair includes a first electrode and second electrode supported on the substrate essentially as described above. In another embodiment, a pad of resistive material may optionally be disposed between the first electrode and second electrode. A 2.5% solution of 3-glycidoxypropyltrimethoxysilane (GOPS) is made up in isopropanol (20%), water (2.5%) and acetic acid (10%). The pH is adjusted to 1.0 using 6N HCl. The solution is allowed to hydrolyze for one hour before adding 0.25 ml of triethylamine. The resistance wafer is then immersed in the GOPS for 3 hours or overnight. The resulting silanized wafer is then cured in an oven at 100° C. for 3 hours. The GOPS surface is then oxidized with 0.1% sodium periodate solution in water (25%) and acetic acid (50%) for 30 minutes and then washed in water for 5 minutes.

For each target of interest, a complementary oligonucleotide probe that has a 5'-amine attached (can be synthesized by commercial vendors or prepared according to methods well known in the art) is obtained. The probes are then bound to the wafer surface via the 5'-amine moiety, e.g. by spotting the probes onto the wafer surface under appropriate conditions at sites located between the first electrode and second electrode of each electrode pair to result in an array of features on the wafer surface. The probes may be incubated at 100 uM with the GOPS-derivatized wafer in a buffer commercially available as Array-it™ ( TeleChem International, Inc., Sunnyvale, Calif.). The incubation is at 4° C., overnight. The wafer is then incubated in 0.01 M sodium periodate in 0.1 M phosphate buffer pH 6.0 for 30 minutes. The wafer is washed three times in PBS (phosphate buffered saline).

Contacting the Device with the Sample

Samples containing oligonucleotide targets are obtained and conjugated with biotin according to published methods (can be synthesized by commercial vendors). The resulting samples containing the biotin-conjugated oligonucleotide targets are applied to the surface of the array in a buffered solution and allowed to hybridize to the arrayed probes according to methods known in the art (Lockhart et al., Nature Biotech. (1996) 14; 1675-1680, Cronin et al., Human Mutation (1996) 7; 244-255). Typical target hybridization conditions range from 1 to 100 nM nucleic acid target in a buffer containing 3 to 6×SSPE (6×SSPE contains; 0.9 M NaCl, 60 mM NaH2PO4, 6 mM EDTA). The hybridization buffer may also contain CTAB (cetyltrimethylammonium bromide) at concentrations ranging from 5 to 10 mM or detergents such as SDS (sodium dodecyl sulfate) or Triton X-100 ranging in concentration from 0.005% to 0.01%. The hybridization is carried out at 30 to 60° C. for 20 minutes to 12 hours. After hybridization, the array is washed with a buffered solution containing 3 to 6×SSPE containing 0.005 to 0.02% SDS at 20 to 60° C. to remove the unhybridized target material. The exact hybridization conditions will depend upon the probe length and the specific application being employed.

The label in this example is 1.4 nm gold nanoparticles (Nanogold™ particles, from Nanoprobes, Inc., New York). Unlike colloidal gold (which adsorbs to molecules) the gold nanoparticles are covalently attached to compounds at specific sites under mild buffer conditions. For example, monomaleimido Nanogold particles label thiols, and mono-NHS (N-hydroxy-succinimide) Nanogold™ particles label amines. As a result Nanogold™ particles can be conjugated to any molecule with a suitable reactive group, including oligonucleotides, lipids, peptides, proteins, enzyme inhibitors and small molecules. In this example, Strep-avidin-conjugated 1.4 nm Nanogold™ nanoparticles are obtained from Nanoprobes (NY) and diluted 1:50 in PBS, 0.5% BSA and 1% Triton X-100. The wafers are incubated for 30 minutes then washed extensively for 10 minutes in PBS and then dried.

The Enhancement Reaction

In the enhancement reaction, the 1.4 nm Nanogold™ particles immobilized on the wafer are enhanced with gold or silver (1-5 minutes). The gold nanoparticles nucleate the deposition of gold metal from a solution comprising AuCl, thus increasing the diameter of the 1.4 nm particle to sizes ranging from 2-20 nm in diameter (dependent on development time). These particles have been demonstrated to grow as large as 50 nm or more in diameter. The enhancement reaction modifies the gold nanoparticles to produce or alter an observable property of the feature, indicating the presence of the label. The enhancement reagent includes solutions of AuCl in the presence of a catalyst and initiator. The enhancement kit has four reagents: Reagent A is an enhancer; reagent B is an activator; reagent C is an initiator; and reagent D is buffer. In use, equal volumes of reagent A and B are combined, then followed by an equal volume of C, followed by reagent D, according to the instructions.

Alternate enhancement reagents include the use of silver enhancer solution which is composed of $AgNO_3$ and hydroquinone. The silver enhancer is replaced every 2 or 3 minutes to avoid formation of silver particulate in solution. The enhancing reagents should be selected according to the label used.

Measuring the Observable

The wafer is rinsed thoroughly and dried. The wafer is then placed in a microarray reader. The microarray reader includes a measurement apparatus suitable for measuring the desired observable property, e.g. resistance (in which case the measurement apparatus may be a resistance measuring circuit which is contained in the microarray reader. The microarray reader also includes an interface adapted to connect to the microarray wafer. The microarray reader includes a microprocessor programmed to interrogate the microarray via the interface, using the measurement apparatus. The microcomputer is programmed to deliver address signals to the addressing circuitry on the microarray wafer to select features to be interrogated. A signal corresponding to the measured observable property is received by the measurement apparatus, which outputs data to the microprocessor. The data may then be analyzed. For example, resistance between the two electrodes of each feature is measured before and after hybridization and enhancement of the gold nanoparticle. The resulting data isis analyzed to indicate specific binding of the target to the complementary probe bound to the resistive pad. Alternatively, another suitable measurable observable property, such as conductance, capacitance, impedance, current, potential, transmission of a signal between the two electrodes, or the like, may be measured by suitable measurement apparatus.

While the foregoing embodiments of the invention have been set forth in considerable detail for the purpose of making a complete disclosure of the invention, it will be apparent to those of skill in the art that numerous changes may be made in such details without departing from the spirit and the principles of the invention. Accordingly, the invention should be limited only by the following claims.

All patents, patent applications, and publications mentioned herein are hereby incorporated by reference in their entireties.

What is claimed is:

1. A method of detecting a target in a sample, the method comprising:
   (a) contacting a microarray with the sample, the microarray comprising a plurality of features disposed on a substrate, each feature comprising a first electrode disposed on the substrate, a second electrode disposed on the substrate, a pad of resistive material disposed on the substrate between the first electrode and the second electrode, said pad of material comprising a material selected from the group consisting of carbon thin film, metal thin film, metal nitride, nichrom (NiCr), tantalum nitride ($Ta_2N$), silicon chrome, and metal oxide, and a probe supported on the pad of resistive material, the substrate comprising integrated addressing circuitry in operable relation to each of the plurality of features;
   (b) applying a source of metal ions to the plurality of features to result in metal deposited between the first electrode and the second electrode of said features where the target is present, said metal providing a change in an observable property of at least one of the plurality of features;
   (c) providing a signal to the addressing circuitry to select one of the plurality of features to be interrogated; and
   (d) measuring the observable property at the selected feature to detect the target.

2. The method of claim 1 wherein the observable property is selected from the group consisting of resistance, impedance, conductance, capacitance, current, potential, and transmission of a signal between the two electrodes.

3. The method of claim 1, further comprising (g) attaching a label to the target prior to applying the source of metal ions.

4. The method of claim 3, wherein the label comprises a nanoparticle selected from the group consisting of a gold nanoparticle and a silver nanoparticle.

5. The method of claim 4, wherein applying the source of metal ions results in deposition of the metal onto the nanoparticle.

6. The method of claim 3, wherein the label is attached to the target via a conjugate binding pair selected from the group consisting of biotin-avidin and digoxigenin-antidigoxigenin.

7. The method of claim 1, wherein a plurality of targets are detected.

8. A microarray comprising a plurality of features disposed on a substrate, each feature comprising a first electrode disposed on the substrate, a second electrode disposed on the substrate, a pad of resistive material disposed on the substrate between the first electrode and the second electrode, and a probe supported on the pad of resistive material, the substrate comprising integrated addressing circuitry in operable relation to the features, the addressing circuitry operable to select a given feature to allow interrogation of the selected feature, and the pad of resistive material comprising a material selected from the group consisting of carbon thin film, metal thin film, metal nitride, nichrom (NiCr), tantalum nitride ($Ta_2N$), silicon chrome, and metal oxide.

9. The microarray according to claim 8, wherein the pad of resistive material comprises a plurality of segments with fissures between the segments.

10. The microarray according to claim 8, wherein the substrate comprises measurement circuitry in electrical communication with the addressing circuitry, the measurement circuitry being operable to interrogate the given feature selected by the addressing circuitry.

11. The microarray according to claim 8, wherein the substrate comprises integrated circuitry for storage of data in operable relation to the addressing circuitry.

12. The microarray according to claim 8, wherein the probe comprises at least one of the group consisting of polypeptides, polynucleotides, glycoproteins, polysaccharides, hormones, growth factors, peptidoglycans, ribonucleotides, deoxyribonucleotides, modified nucleosides, peptide nucleic acids, and oligomeric nucleoside phosphonates.

13. The microarray of claim 8, wherein each of the plurality of features comprises a different probe.

14. The microarray of claim 8, wherein the microarray comprises at least one reference feature in operable relation to the addressing circuitry.

15. The method of claim 1, further comprising:
   repeating steps (c) and (d) to selectively interrogate another of the plurality of features; and
   analyzing the results obtained from step (d) to detect the target.

16. A microarray comprising a plurality of features disposed on a substrate, each feature comprising a first electrode disposed on the substrate, a second electrode disposed on the substrate, a pad of resistive material disposed on the substrate between the first electrode and the second electrode, and a probe supported on the pad of resistive material, the substrate comprising integrated addressing circuitry in operable relation to the features, the addressing circuitry operable to select a given feature to allow interrogation of the selected feature, and the pad of resistive material comprising a plurality of segments with fissures between the segments.

17. The microarray according to claim 16, wherein the pad of resistive material comprises a material selected from the group consisting of carbon thin film, metal thin film, metal nitride, nichrome (NiCr), tantalum nitride ($Ta_2N$), silicon chrome, and metal oxide.

18. The microarray according to claim 16, wherein the probe comprises at least one of the group consisting of polypeptides, polynucleotides, glycoproteins, polysaccharides, hormones, growth factors, peptidoglycans, ribonucleotides, deoxyribonucleotides, modified nucleosides, peptide nucleic acids, and oligomeric nucleoside phosphonates.

19. The microarray of claim 16, wherein each of the plurality of features comprises a different probe.

* * * * *